United States Patent [19]
Yabe et al.

[11] Patent Number: 5,514,074
[45] Date of Patent: May 7, 1996

[54] ENDOSCOPE APPARATUS OF AN ENDOSCOPE COVER SYSTEM FOR PREVENTING BUCKLING OF AN ENDOSCOPE COVER

[75] Inventors: Hisao Yabe, Hachioji; Yoshihiro Iida, Tama; Akira Suzuki; Hideo Ito, both of Hachioj; Yoshio Tashibo, Hiro; Minoru Yamazaki; Osamu Tamada, both of Hachioji, all of Japan

[73] Assignee: Olympus Optical Co., Ltd., Tokyo, Japan

[21] Appl. No.: 391,464

[22] Filed: Feb. 21, 1995

Related U.S. Application Data

[63] Continuation of Ser. No. 34,409, Mar. 19, 1993, abandoned.

[30] Foreign Application Priority Data

| Feb. 12, 1993 | [JP] | Japan | 5-004275 U |
| Feb. 12, 1993 | [JP] | Japan | 5-004276 U |
| Feb. 12, 1993 | [JP] | Japan | 5-004277 U |

[51] Int. Cl.⁶ ................................ A61B 1/00
[52] U.S. Cl. .......................... 600/121; 600/123
[58] Field of Search .................. 128/4, 6; 604/282; 600/121, 123, 124, 125, 122

[56] References Cited

U.S. PATENT DOCUMENTS

| Re. 34,110 | 9/1992 | Opie . |
| 3,162,190 | 12/1964 | Del Gizzo . |

(List continued on next page.)

FOREIGN PATENT DOCUMENTS

| 0184778 | 6/1986 | European Pat. Off. . |
| 0310515 | 4/1989 | European Pat. Off. . |
| 0338567 | 10/1989 | European Pat. Off. . |
| 0341718 | 11/1989 | European Pat. Off. . |
| 0341719 | 11/1989 | European Pat. Off. . |
| 0349479 | 1/1990 | European Pat. Off. . |
| 0440252 | 8/1991 | European Pat. Off. . |
| 0440254 | 8/1991 | European Pat. Off. . |
| 0444429 | 9/1991 | European Pat. Off. . |
| 3909290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |

(List continued on next page.)

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

A cover system endoscope apparatus in which an insert part cover sheath for isolating the insert part of a cover endoscope is airtightly connected to a distal end constructive part of a tip part of an insert part cover. The insert part cover sheath is composed of a soft resin such as polyurethane exhibiting an excellent chemical resistance and a relatively high flexibility. The tip side of the cover sheath is connectively covered on an outer peripheral edge of the rear end of the distal end constructive part. The insert part cover sheath is formed with a forceps inlet on its near-at-hand side. Connected airtightly thereto is an endoscope manipulation part fixing mouth part having an expansion tube mouth for connecting an expansion tube and further a connecting part connected to a cover holding tool. An opening of an endoscope insert channel provided in an interior of the insert part cover sheath is formed on the near-at-hand side of the endoscope manipulation part fixing mouth part. The tip of the endoscope manipulation part fixing mouth part is connected to the distal end constructive part of the cover. Protruded are conduits such as air and water supply conduits and a channel communicating with a forceps outlet. These conduits are each formed of a soft resin such as PTFE exhibiting a low flexibility but a relatively high rigidity. A flexural rigidity when combining these conduits is larger than a flexural rigidity of the insert part cover sheath.

10 Claims, 13 Drawing Sheets

U.S. PATENT DOCUMENTS

| | | | |
|---|---|---|---|
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie et al. | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,947,827 | 8/1990 | Opie et al. | 128/4 |
| 4,991,564 | 2/1991 | Takahashi et al. | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |

FOREIGN PATENT DOCUMENTS

| | | |
|---|---|---|
| 2-57228 | 2/1990 | Japan . |
| 2-54734 | 11/1990 | Japan . |
| 3-13105 | 2/1991 | Japan . |
| 3-37030 | 2/1991 | Japan . |
| 3-37029 | 2/1991 | Japan . |
| 3-29635 | 2/1991 | Japan . |
| 3-29634 | 2/1991 | Japan . |
| 3-221024 | 9/1991 | Japan . |
| 3-101906 | 10/1991 | Japan . |
| 3-101907 | 10/1991 | Japan . |
| 3-101905 | 10/1991 | Japan . |
| 3-101904 | 10/1991 | Japan . |
| 3-101903 | 10/1991 | Japan . |
| 3-101902 | 10/1991 | Japan . |
| 3-101901 | 10/1991 | Japan . |
| 4-325138 | 11/1992 | Japan . |

ENDOSCOPE APPARATUS OF AN ENDOSCOPE COVER SYSTEM FOR PREVENTING BUCKLING OF AN ENDOSCOPE COVER

This application is a continuation of application Ser. No. 08/034,409 filed Mar. 19, 1993, now abandoned.

BACKGROUND OF THE INVENTION

1. Field of the Invention

The present invention relates to an endoscope apparatus of an endoscope cover system for installing an endoscope into an endoscope cover expanded by an endoscope cover expander.

2. Description of the Related Art

In recent years, the endoscope apparatus has been widely employed in the medical field. The endoscope apparatus utilized in the medical sector is in some cases incapable of providing adequate viewing due to a body fluid adhered to a viewing window formed in the tip of an insert part when inserted into a living body. For this reason, an air or water supply conduit is provided for removing the body fluid adhered to the viewing window by flushing a fluid over the viewing window. Some of the endoscope apparatuses are equipped with a suction conduit for sucking and discharging the useless body fluid.

Further, some are provided with a forceps channel (treatment tool channel) whereby the tissues can be extracted by means of a living-body examining forceps, or a medical treatment can be conducted by a treatment tool.

In the endoscope apparatus provided with the conduits such as the air supply conduit or the like and the forceps channel, cleaning and antibacterial treatment are effected for surely preventing infectious diseases, etc. The complete antibacterial treatment and cleaning, however, are time-consuming. There arise problems in which a using efficiency of the endoscope decreases, and workings such as the antibacterial treatment are troublesome.

Under such circumstances, there is proposed a cover system endoscope apparatus requiring no cleaning and no antibacterial treatment by covering the endoscope itself in use with an endoscope cover to keep the endoscope itself clean.

For instance, Japanese Patent Laid-Open No. 3-29634 discloses a cover system for covering the insert part of the endoscope by inserting it into a cover (sheath). For facilitating an installation and removal of the endoscope insert part into and from the cover, the air is supplied from a cover expander into the insert part cover into which the endoscope insert part is inserted.

The insert part cover is disposable so as not to form a hole in the cover sheath due to buckling when handled in the form of a single unit or not to be ruptured when used, and is composed of a resinous tube of polyurethane for providing strength. Further, in some types of endoscope apparatuses, the insert part cover includes a channel for inserting the forceps and conduits for supplying the air and water.

Those soft resinous tubes are formed of soft materials as are possible to prevent an imbalance of flexibility in the cover endoscope inserted into the cover. The tube is, however, required to have sufficient rigidity so as to not break a cavity of the tube itself or not cause buckling. The cover as a whole has a certain degree of flexural rigidity.

That is, the insert part cover is, when the endoscope is not inserted therein, easy to break and fold. Once the cover has a tendency of being folded, this portion is repeatedly folded with the result that pin holes are formed in the cover sheath. The cover is then unusable. For enhancing the durability, the cover sheath is made resistant against folding by increasing both a thickness of the cover sheath and a hardness thereof.

The requirement of the disposable endoscope cover, however, may be a durability for one disease case. A larger thickness of the cover sheath than needed leads to a futility of costs for materials. This causes an increase in the price of the product.

Further, the enhancement of the hardness provides a high resistance against collapse but implies an easy-to-buckle state. The enhancement thereof is also apt to change the well-balanced flexibility of the endoscope according to the object and therefore worsen the insertability thereof.

By the way, the maximum bending angle of the endoscope is generally adjusted in the course of manufacturing a single unit of an endoscope. One exemplification may be a known endoscope of such a system that a plurality of bending members are connected with rivets, and a bending wire fixed to the tip part is pulled in by a near-at-hand manipulation part, thus controlling the flexure. In this case, a stopper is incorporated in a pull-in device to which the wire is connected internally of the manipulation part. The stopper is fixed in a maximum-bending-angle position while measuring a bending angle of the tip part. A maximum bending angle of the endoscope is set in this manner. Hence, when the angle is set once, the user is unable to simply alter the angle.

The endoscope with the maximum bending angle set in this way is installed into the insert part cover. When controlling the flexure, a bendable part of the endoscope undergoes a resistance of flexural rigidity of the cover described above. The bendable part cannot be therefore bent up to the maximum bending angle set in the single unit of endoscope. The maximum bending angle of the endoscope is set to an operable angle with respect to a target organ, depending on a type of the endoscope. Therefore, if the maximum bending angle required is not obtained in a state of combination of the endoscope and the insert part cover as described above, this causes a problem wherein the operability of the endoscope declines.

SUMMARY OF THE INVENTION

It is a primary object of the present invention to provide a cover system endoscope apparatus capable of preventing buckling of an endoscope cover with a channel, being offered at a low price and exhibiting excellent operability while being easy to handle.

It is another object of the present invention to provide a cover system endoscope apparatus capable of exhibiting excellent operability and obtaining a maximum bending angle needed in a state of combination of an endoscope and an endoscope cover by adjusting the maximum bending angle of the tip part of the endoscope so that the maximum bending angle of the tip part of a cover endoscope of the cover system endoscope apparatus becomes a predetermined bending angle.

Briefly, according to one aspect of this invention, there is provided a cover system endoscope apparatus comprising an endoscope and an endoscope cover for covering the endoscope. The endoscope cover includes a distal end constructive part, a proximal end constructive part and a soft tubular part through which the distal end constructive part and the proximal end constructive part are airtightly connected. The tubular part has a soft channel tube provided in the interior thereof. A rigidity of the channel tube is set larger than a rigidity of the tubular member.

Other objects and advantages of the present invention will become apparent during the following discussion.

BRIEF DESCRIPTION OF THE DRAWINGS

FIG. 1 is a view illustrating a whole configuration of a cover system endoscope apparatus including a cover endoscope;

FIG. 2 is a view showing a constructive appearance of the cover endoscope;

FIG. 3 is a view illustrating a profile of a tip part of the cover endoscope;

FIG. 4 is a view illustrating a profile of a tip part of an insert part cover;

FIG. 5 is a sectional view showing a configuration of the principal portion of the cover endoscope;

FIGS. 6(a) and 6(b) are explanatory views showing maximum bending angles of a cover endoscope and of a single unit of endoscope;

FIGS. 7(a)–7(b) are explanatory views showing how a universal cord cover is covered on a universal cord;

FIG. 8 is an explanatory view showing an overcoat tube covering the cover sheath during storage of the covering section.

FIG. 9 is a sectional view illustrating a configuration of a flexure control device and a flexure control knob;

FIG. 10 is an explanatory view showing a configuration of a modified example of the universal cord cover;

FIG. 12 is a view illustrating an appearance of the tip part of the insert part cover;

FIG. 13 is a view showing a profile of the tip part of the insert part cover;

FIG. 14 is a sectional view showing a configuration of the principal portion of the cover endoscope;

FIGS. 15 and 16 are related to a fourth embodiment;

FIG. 15 is a view illustrating a profile of the tip part of the insert part cover.

DETAILED DESCRIPTION OF THE PREFERRED EMBODIMENTS

Figure 1:
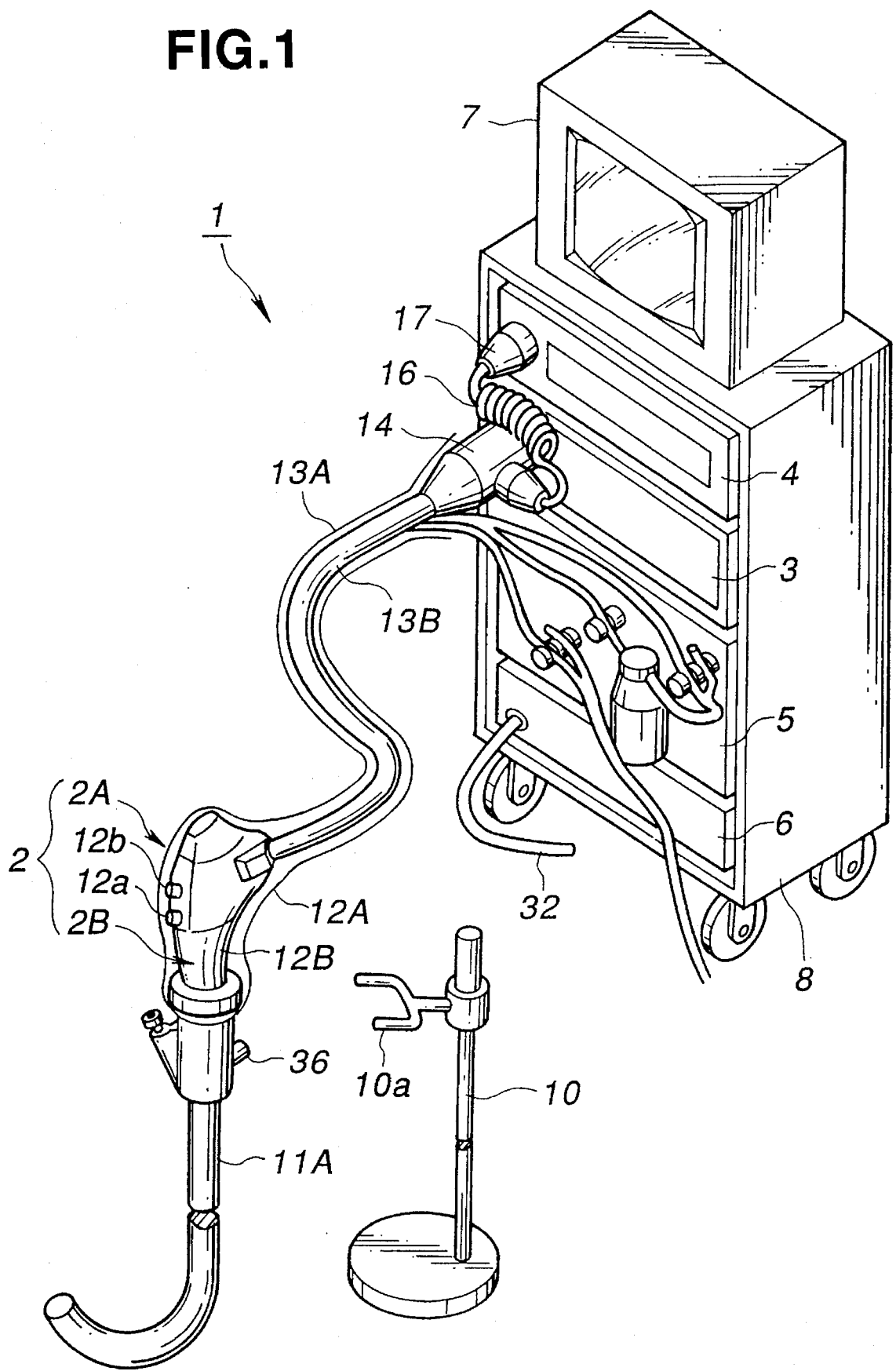
FIGS. 1 through 10 are related to a first embodiment.

A first embodiment will hereafter be discussed. As illustrated in FIG. 1, an endoscope equipment of an endoscope cover system (hereafter simply referred to as a cover system endoscope equipment) 1 is constructed of an endoscope cover system endoscope apparatus (hereafter simply called a cover system endoscope apparatus) 2 with a channel, a light source unit 3, a video processor 4, a fluid control unit 5, an endoscope cover expander (hereafter simply referred to as a cover expander) 6 with a channel and a monitor 7. The endoscope apparatus 2 consists of a channeled endoscope cover (hereafter simply referred to as a cover) 2A and a cover endoscope 2B covered with this cover. The light source unit 3 supplies illumination light to this cover endoscope 2B. The video processor 4 processes signals with respect to an imaging means built in the cover endoscope 2B. The fluid control unit 5 supplies the air and water via a tube of the cover 2A. The cover expander 6 is employed for covering the cover endoscope with the cover 2A. The monitor 7 displays an image signal processed by the video processor 4. A cart 8 encases the light source unit 3, the video processor 4, the fluid control unit 5 and the cover expander 6. The monitor 7 is mounted on the upper surface of the cart 8.

The following is a characteristic when effecting an examination by the endoscope. The clean cover endoscope 2B is covered with the clean cover 2A. After the examination, the cover 2A is disposed of. Subsequently, the cover endoscope 2B is covered with a new clean cover 2A and thus repeatedly used.

Figure 2:
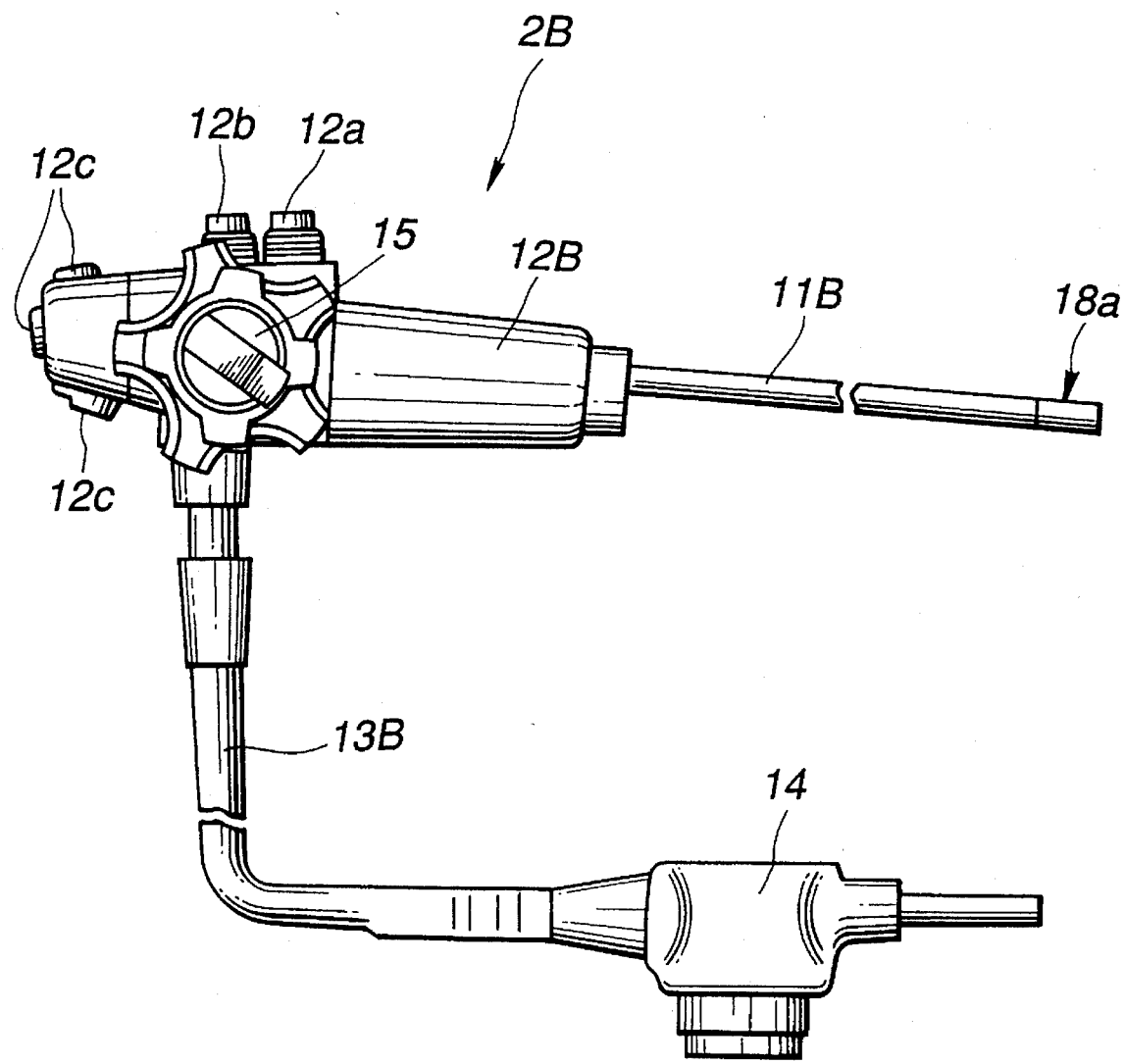

As shown in FIG. 2, the cover endoscope 2B comprises an endoscope insert part (hereafter simply called an insert part) 11B, and an endoscope manipulation part (hereafter simply referred to a manipulation part) 12B and a universal cord 13B. The insert part 11B is elongate and exhibits flexibility. The manipulation part 12B is formed at the proximal end of this insert part 11B. The universal cord 13B extends from the side portion of this manipulation part 12B. A connector 14 provided at the terminal of this universal cord 13B is detachably connectable to the light source unit 3. Because the connector 14 is connected to this light source unit 3, a lamp provided in the interior of the light source unit 3 supplies the illumination light to the terminal of an unillustrated light guide inserted through the universal cord 13B. Further, a cable 16 extends from the connector 14. A signal connector 17 provided at the terminal of this cable 16 is detachably connectable to the video processor 4 (see FIG. 1). Moreover, an antibacterial agent is coated on the outer surface of the insert part 11B. Note that an application of the antibacterial agent of the insert part 11B is not limited to the coating on the outer surface thereof but may be infused into a material of the outer surface.

The manipulation part 12B includes a flexure control knob 15 provided on the side opposite the side surface from which the proximal end of the universal cord 13b protrudes. A bendable portion of a tip part 18a formed at the tip of the insert part 11B is bendable by manipulating this flexure control knob 15. The manipulation part 12B is also provided with an air/water supply switch 12a, a suction switch 12b and an image changeover switch 12c, etc. The air/water supply, suction and image freezing can be performed by operating the respective switches.

Figure 3:
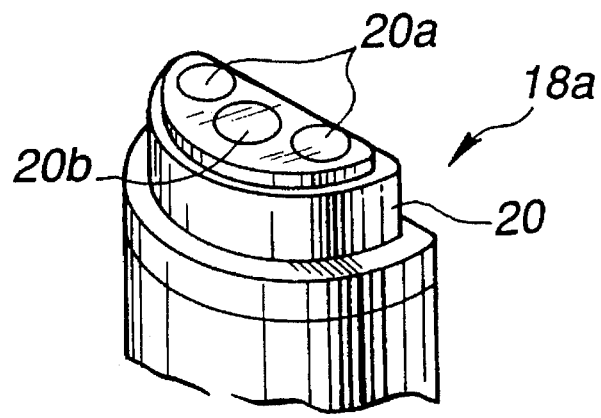

The tip part 18a of the cover endoscope 2B is, as illustrated in FIG. 3, formed of a distal end constructive part 20 assuming a semi-circular shape in section. The end surface of the distal end constructive part 20 is provided with an illumination optical system 20a and a viewing optical system 20b.

On the other hand, the cover 2A is, as shown in FIG. 1, constructed of an insert part covering section 11A, a manipulation part covering section 12A and a universal cord covering section (hereafter called a cord cover) 13A which serve to cover respectively the insert part 1B, the manipulation part 12B and the universal cord 13B of the cover endoscope 2B.

Figure 4:
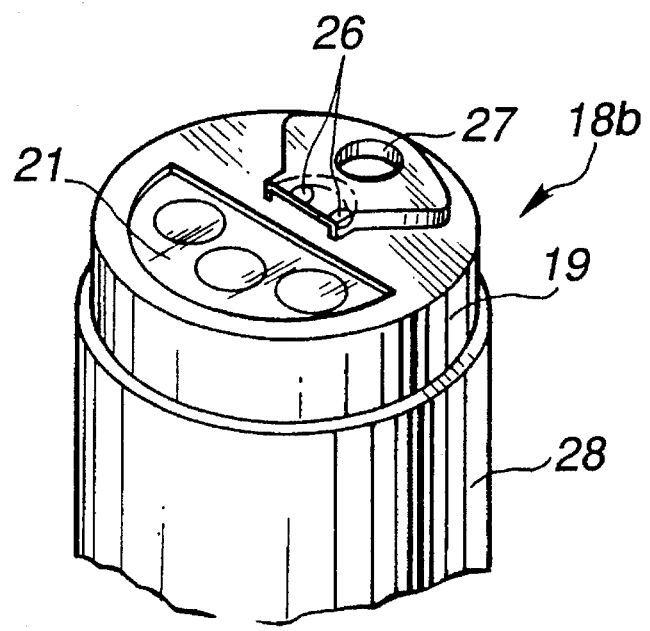

A tip part 18b of the insert part covering section 11A is, as illustrated in FIG. 4, formed of a distal end constructive part 19. The tip part 18b includes a transparent cover viewing window 21 corresponding to the semi-circular shape of the tip part 18a of the cover endoscope 2B shown in FIG. 3. The tip part 18b further includes air/water supply nozzles 26 opened to the cover viewing window 21 and a forceps outlet 27. Connected airtightly to this distal end constructive part 19 is an insert part cover sheath 28 for isolating the insert part 11B of the cover endoscope 2B from the external environment.

The illumination light emitted from the light source unit 3 is led to one end surface of the light guide (not illustrated). The illumination light, as illustrated in FIG. 3, outgoes from the end surface of the illumination optical system 20a of the distal end constructive part 20 of the insert part 11B toward a front subject via the cover viewing window 21 formed at the tip part of the insert part covering section 11A. The light returned from the subject such as a diseased part is incident on the viewing window of the viewing optical system 20b provided adjacent the illumination optical system 20a through the cover viewing window 21.

Figure 5:
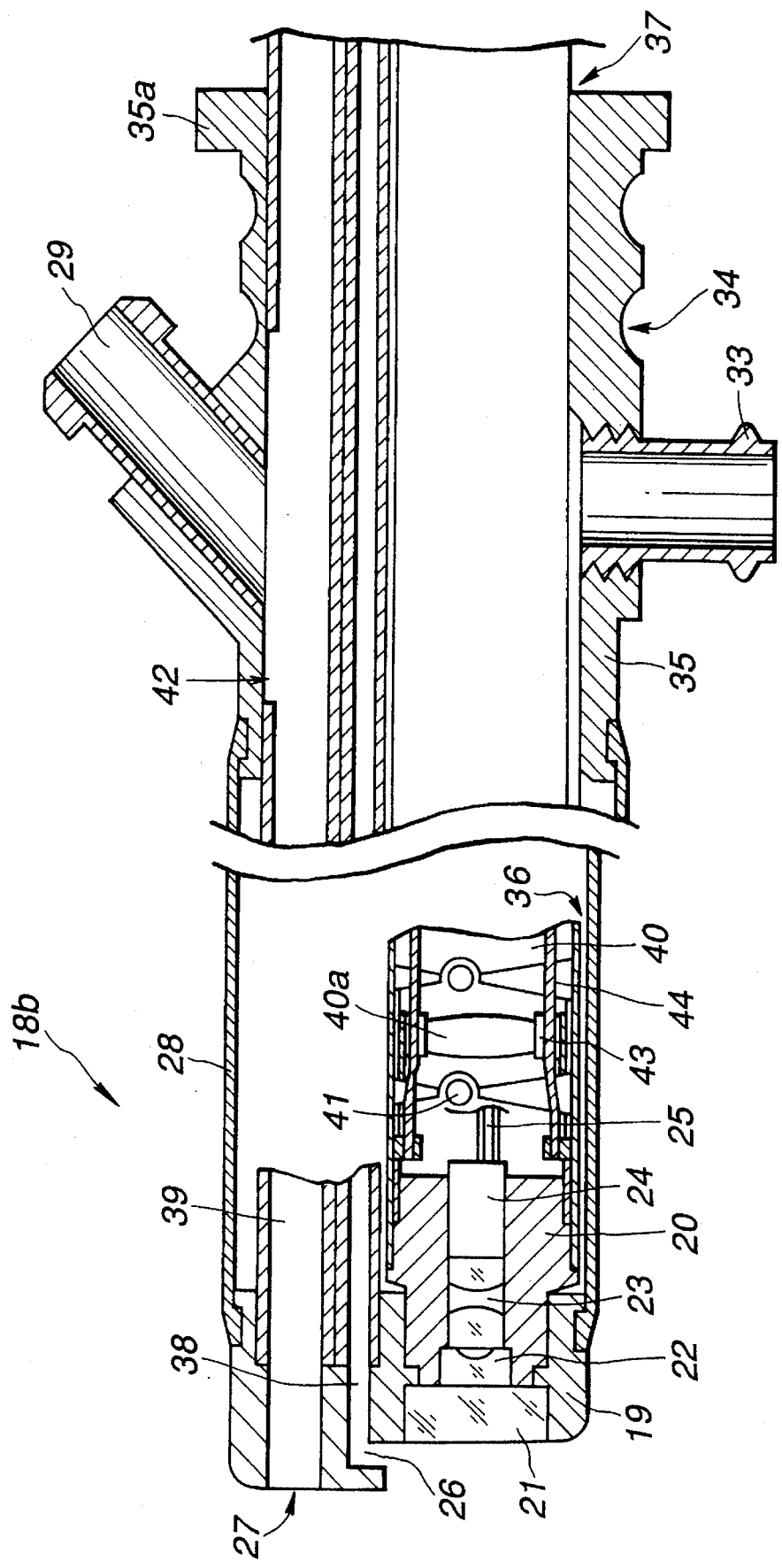

The viewing optical system 20b consists, as depicted in FIG. 5, of an objective optical system 23 so attached to the viewing window 22 provided inwardly of the cover viewing window 21 so as to confront this window 21. An optical image is formed on a focal plane of this objective optical system 23.

A CCD 24 is disposed on this focal plane. The optical image formed thereon is photoelectrically converted. The converted signal is transmitted to the video processor 4 via signal cables 25, 16 inserted through the insert part 11B and the universal cord 13B. After undergoing signal processing, a standard video signal is generated. This video signal is inputted to the monitor 7, whereby an image of the subject is displayed on a display screen.

The insert part cover sheath 28 is composed of a soft resin such as polyurethane exhibiting an excellent chemical resistance and a relatively high flexibility (e.g., minor diameter: 10 mm, and thickness: 0.2 mm). The top part thereof is connectively covered on the outer peripheral edge of the rear end of the distal end constructive part 19. A forceps insert port 29 is formed in a predetermined location of a near-at-hand portion of the insert part cover sheath 28. Connected airtightly to this near-at-hand portion is an endoscope manipulation part fixing mouth part 35 including an expansion mouth 33 for connecting an expansion tube 32 (see FIG. 1) and further a connection part 34 to be connected to a cover holding tool 10.

A near-at-hand portion 35a of this endoscope manipulation part fixing mouth part 35 is formed with an opening 37 of an endoscope insert channel 36 provided inwardly of the insert part cover sheath 28. Further, the distal end of the endoscope manipulation part fixing mouth part 35 is connected to the distal end constructive part 19 of the cover. Protruded are conduits such as an air supply conduit 38 (e.g., minor diameter: 1.2 mm, and thickness: 0.3 mm), a water supply conduit (though not illustrated, e.g., minor diameter: 1.2 mm, and thickness: 90.3 mm) each communicating with the air/water supply nozzle 26 and a channel 39 (e.g., minor diameter: 3.2 mm, and thickness: 0.5 mm) communicating with the forceps outlet 27. The ends of the near-at-hand portions of the air supply conduit 38 and the water supply conduit are herein connected to not illustrated air/water supply sources. These conduits are each composed of a soft resin such as PTFE or the like exhibiting a low flexibility and a relatively high flexural rigidity. The flexural rigidity when combining these conduits is larger than a flexural rigidity of the insert part cover sheath 28.

The tip of the insert part 11B of the cover endoscope 2B is provided with a bendable part 40a. The bendable part 40a is formed by connecting a plurality of non-circular tubular bendable members 40 with rivets 41 in continuation from the distal end constructive part 20. A wire insertion restrictor 43 protruding inward is provided in the bendable part 40 correspondingly in the bending direction. A flexure control wire 44 connected to the distal end constructive part 20 of the cover endoscope 2B is inserted into an interior of this wire insertion restrictor 43. A rear end of the flexure control wire 44 is connected to a bending device incorporated into the manipulation part 12B, which will be mentioned later. This bending device includes, though not shown, a known stopper for regulating a bending angle, thereby determining the maximum bending angle of the tip part 18 of the cover endoscope 2B.

Figure 6:
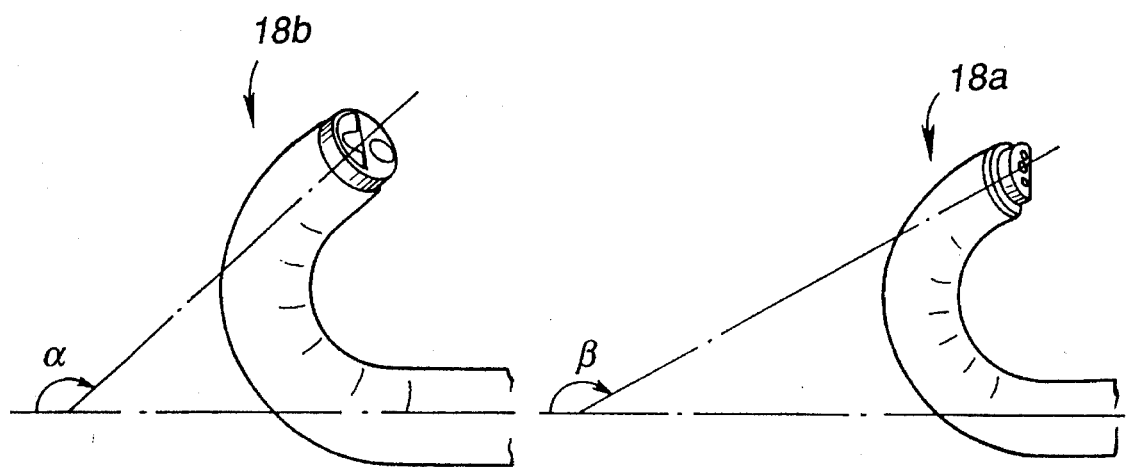

FIG. 6(a) shows an external appearance of the tip part of the cover endoscope with the insert part covering section 11A when bent at the maximum. FIG. 6(b) shows that of a single unit of endoscope 2B when bent at the maximum. The maximum bending angle $\beta$ of the single cover endoscope 2B is set larger than the maximum bending angle $\alpha$ required for the endoscope when covered with the insertion part covering section 11A. A value obtained by $\beta-\alpha/\alpha$ this time is, though different depending on a magnitude of the flexural rigidity of the insert part covering section 11A to be assembled, desirably about 5~20%. For instance, $\beta$ is set at 170° in this case. When assembled in the insert part covering section 11A, the maximum bending angle becomes 160°.

Figure 7:
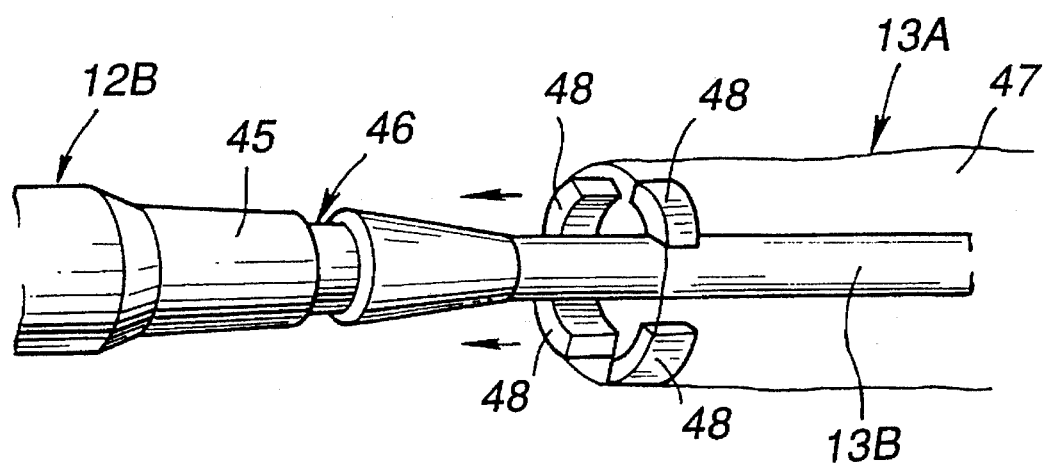
Figure 7:
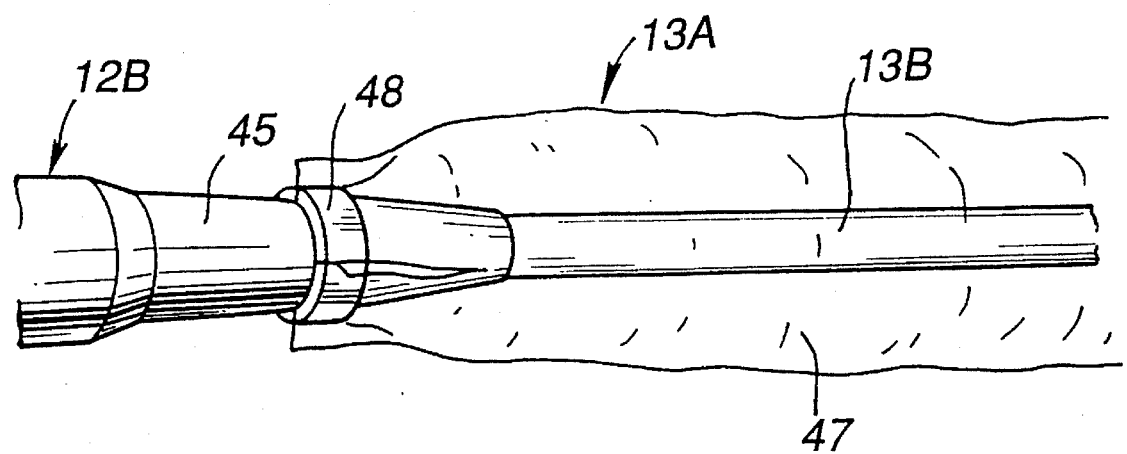

FIG. 7 is an enlarged view of the connecting part of the cord cover 13A. FIG. 7(a) shows a state before being connected. FIG. 7(b) shows a state after being connected.

As illustrated in FIG. 7(a), the universal cord 13B on the side of the manipulation part 12B is connected via a connecting proximal part 45 to the manipulation part 12B. A small-diameter fixing groove 46 is cut in some of the outer peripheral surface of the connecting proximal part 45 so as to extend along the entire periphery thereof.

On the other hand, the cord cover 13A consists of a cover 47 composed of a cylindrical soft plastic material and fixing members 48 provided on the inner peripheral surface of the end part thereof. The fixing members are a plurality of segments, each assuming a fan-shape in section, of an annular magnetic part having a minor diameter smaller than a major diameter of the fixing groove 46 on the side of the universal cord 13B. The fixing members 48 are allocated substantially uniformly along the inner peripheral surface of the cover 47. An outer periphery of each of the fixing members 48 is bonded to the inner surface of the cover 47. Then, as illustrated in FIG. 7(b), the fixing members 48 are fitted in the fixing groove 46, thus making a magnetic connection.

Figure 8:
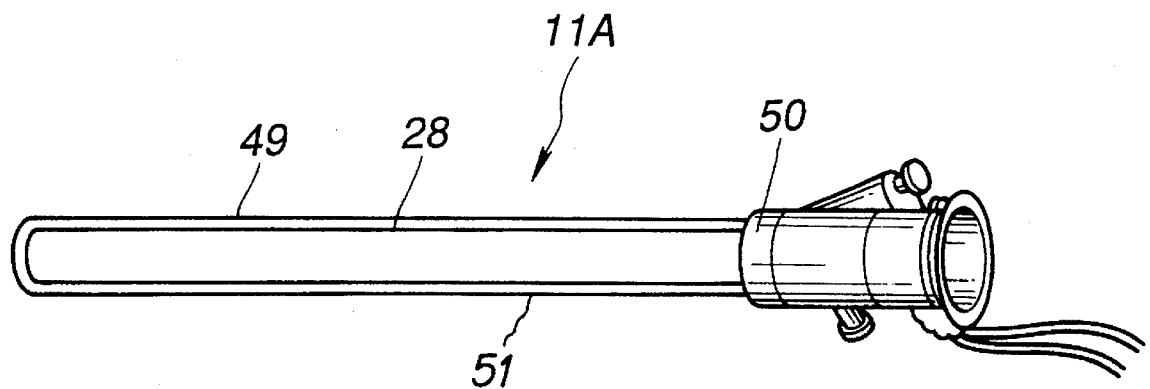

As illustrated in FIG. 8, when storing the insert part covering section 11A, the cover sheath 28 is covered with an overcoat tube 49. The cover sheath 28 is connectively secured to the endoscope manipulation part fixing mouth part 35 through an opening unit 50 provided on the near-at-hand side of the overcoat tube 49. A lubricating material 51 (e.g., xylocain Jelly) employed for improving the insertability of the endoscope is sealed between the cover sheath 28 and the overcoat tube 49.

Figure 9:
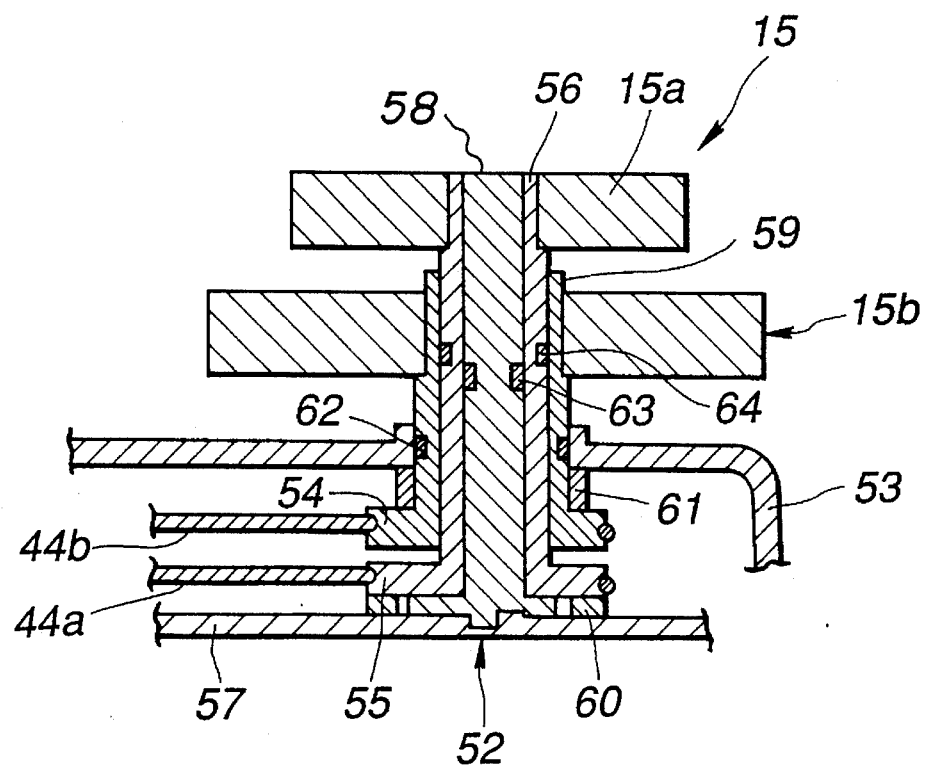

FIG. 9 is a sectional view showing the flexure control device 52 incorporated into the body of the manipulation part 12B and the flexure control knob 15. A pair of upper and lower pulleys 54, 55 are disposed in a casing 53 of the manipulation part 12B. The lower pulley 55 is formed integrally on the proximal end portion of a first cylindrical rotary shaft 56. One manipulation wire 44a described above is wound on the pulley 55. The first rotary shaft 55 is axially rotatably supported on a support shaft 58 protecting from a proper base plate 57 provided inwardly of the casing 53. The tip of this first rotary shaft 56 is protruded externally of the casing 53. A first flexure control knob 15a is fitted in a location apart from the casing 53.

Further, the upper pulley 54 is formed integrally on the proximal part of a second rotary shaft 59 rotatably attached to the first rotary shaft 56. The other manipulation wire 44b is wound on the pulley 54. The tip of the second rotary shaft 59 extends to substantially the same length as the lower surface of the first flexure control knob 15a. A second control knob 15b is fitted to the tip of this second rotary shaft 59.

A first friction ring 60 is provided between the base plate 57 and the pulley 55. A second friction ring 61 is provided between the manipulation part casing 53 and the pulley 54. Seal parts 62, 63, 64 serve to ensure a watertightness between the respective parts.

The following is an explanation of a method of assembling those parts described above.

Firstly, after bonding the transparent viewing window 21 to the distal end constructive part 19, the air supply conduit 38, the water supply conduit (not shown) and the channel 39 (PTFE, minor diameter: 3.2 mm, and thickness: 0.5 mm) are connected to the rear end thereof. A side hole 42 is formed in the rear end portion of the channel 39 adaptively in a position corresponding to the forceps inlet 29 when the endoscope manipulation mouth part 35 is connected. The side hole 42 is longer than the minor diameter of a forceps inlet 29 but shorter than a fitting length of the endoscope manipulation part fixing mouth part 35 and the channel 39.

Secondly, the insert part cover sheath 28 is connectively covered on the outer periphery of the rear end portion of the distal end constructive part 19. The cover sheath 28 is previously worked to a predetermined length corresponding to the length of the insert part of the cover endoscope.

Thirdly, the air supply conduit 38, the water supply conduit (not illustrated) and the channel 39 are inserted into the endoscope manipulation part fixing mouth part 35. The rear end portion of the insert part cover sheath 28 is connected to the front end portion of the endoscope manipulation fixing mouth part 35. At the same time, the respective conduits and the insert part cover sheath 28 are airtightly fixed to the endoscope manipulation part fixing mouth part 35.

It is therefore possible to reduce a scatter in the length of the insert part covering section 11A because of such an assembling step that a distance between the distal end constructive part 19 and the endoscope manipulation part fixing mouth part 35 is determined only by the length of a single part of the insert part cover sheath 28.

The operation of the cover system endoscope apparatus as so constructed will be described.

As in the typical endoscope cover fitting method, the insert part covering section 11A is taken out of an unillustrated cover storage package containing the antibacterial endoscope cover 2A. The insert part covering section 11A is covered with the overcoat tube 49 and can be therefore held by the cover holding tool 10 while keeping an antibacterial state of the cover sheath 28 even when an assistant in an unclean area holds and takes it out. At this moment, the lubricating material 51 sealed in the overcoat tube 49 acts to reduce the friction resistance caused when removing the insert part covering section 11A from the overcoat tube 49. Further, the lubricating material 51 is adhered to the surface of the cover sheath 28 of the insert part covering section 11A.

The cover expander 6 is employed when mounting the insert part covering section 11A on the insert part 11B of the cover endoscope 2B and when removing the insert part 11B from the insert part covering section 11A.

This cover expander 6 is constructed basically of an air supply pump (not illustrated) and an air supply conduit (not illustrated). An opening end of the air supply conduit is provided with a mouth ring for connecting the proximal portion of the expansion tube 32. This cover expander 6 normally continues to supply the air. For this reason, if the function of the cover expander 6 is not used, as illustrated in FIG. 1, the terminal of the expansion tube 32 is not connected to an expansion tube mouth 33 but opens to the outside air for air leakage.

Then, when inserting and removing the cover endoscope 2B into and from the insert part covering section 11A, the terminal of the expansion tube 32 is intruded into the expansion tube mouth 33 and thus airtightly connected thereto by insertion (fitting). The air is fed via the expansion tube mouth 33 into the endoscope insertion channel 36, thereby expanding the endoscope insertion channel 36. It is thus possible to easily insert and remove the endoscope insert part 11B.

When inserting the cover endoscope 2B into this insert part covering section 11A, a flange part of the upper end of the endoscope manipulation part fixing mouth part 35 is held by a semi-circular holding part 10a formed in the cover holding tool 10. In this state, the insert part 11B of the cover endoscope 2B is inserted from the endoscope manipulation part fixing mouth part 35, thus facilitating the installation.

Next, the cord cover 13A is covered from the other end of the connecting proximal part 45 of the universal cord 13B. At this time, the fixing members have already been segmented, and the end portion of the cover 47 is therefore opened wide. Just when the end portion comes to the fixing groove 46, the respective fixing members 48 are so connected by the magnetic force as to be covered on the fixing groove 46, thus fixing the end portion. After the endoscope cover 2A has been mounted, the insert part covering section 11A incorporating the insert part 11B is inserted into the body of the patient.

The maximum bending angle of the tip of the cover system endoscope apparatus 2 is smaller than the maximum bending angle $\beta$ (170°) of the cover endoscope 7 depending on the flexural rigidity of the insert part covering section 11A itself. As a result, the former bending angle comes to the maximum bending angle $\alpha$ (160°) required for the cover system endoscope apparatus 2.

Further, friction resistance is applied on the flexure control knob 15 during the flexure control. The bending angle can be fixed in an arbitrary position. Simultaneously, if the endoscope is mistakenly removed while the tip bendable portion remains bent, the pulley slides on the friction ring, and the flexure is returned to a straight position.

As described above, according to the cover system endoscope equipment 1 in this embodiment, the flexural rigidity when combining the air supply conduit, the water supply conduit and the channel is set larger than the flexural rigidity of the insert part cover sheath. Hence, it is possible to provide a structure in which the insert part covering section is hard to buckle at a low price without losing the flexibility balance of the insert part of the cover endoscope. It is also feasible to improve the operability and ease of handling. Further, the durability of the cover sheath can be restrained down to a level required enough to be disposable. The manufacturing costs can be therefore reduced.

Moreover, the outer peripheral edge of the rear end of the distal end constructive part 19 is covered with the tip part of the cover sheath. The edge is not exposed to the outside and does not therefore cause damage within the body cavity.

Besides, the maximum bending angle of the tip part 18a of the single cover endoscope 2B is set larger than the maximum bending angle needed when assembling the cover 2A. Hence, even if the bending angle is decreased due to the flexural rigidity of the insert part covering section 11A, it is possible to obtain the maximum bending angle required for the cover system endoscope apparatus 2.

Furthermore, friction resistance is applied on the flexure control knob 15 during the flexure control, and the bending angle can be fixed and held in an arbitrary position. At the same time, if the endoscope is pulled out while the bendable portion of the tip part remains bent, the pulley slides on the friction ring. The flexure is returned straight. Hence, the cover endoscope 2B can be removed safely without damaging wall of the body cavity.

Further, the antibacterial coating is applied on the insert part 11B of the cover endoscope 2B. It is therefore feasible to prevent a propagation of various germs during the storage.

Besides, the fixing members 48 are connected by the magnetic force in the fixing groove 46 formed in the connecting proximal part 45 of the universal cord 13B, thus fixing the end portion. The universal cord cover 13A is therefore simply attached and detached. Because of being secured in the fixed groove 46, there is no possibility of contaminating the cover endoscope 2B due to a shift when used.

Further, the insert part covering section 11A is covered with the overcoat tube 49, thereby preventing contamination on the insert part covering section 11A. At the same time, the lubricating material 51 is sealed in the overcoat tube 49. It is thus feasible to readily pull the insert part covering section 11A out of the overcoat tube 49. Furthermore, even after removing the insert part covering section 11A from the overcoat tube 49, the lubricating material is coated on the surface of the cover sheath 28, there is no necessity for applying the lubricating agent each time a part of the cover system endoscope apparatus 2 is inserted into the body cavity. The examination can be quickly conducted.

Note that the universal cord cover 13A is constructed so that the fixing members 48 are connected by the magnetic force in the fixing groove 46 formed in the connecting proximal part 45 of the universal cord 13B. However, the construction is not limited to that above-mentioned. A universal cord cover shown in FIG. 10 may be available.

Figure 10:
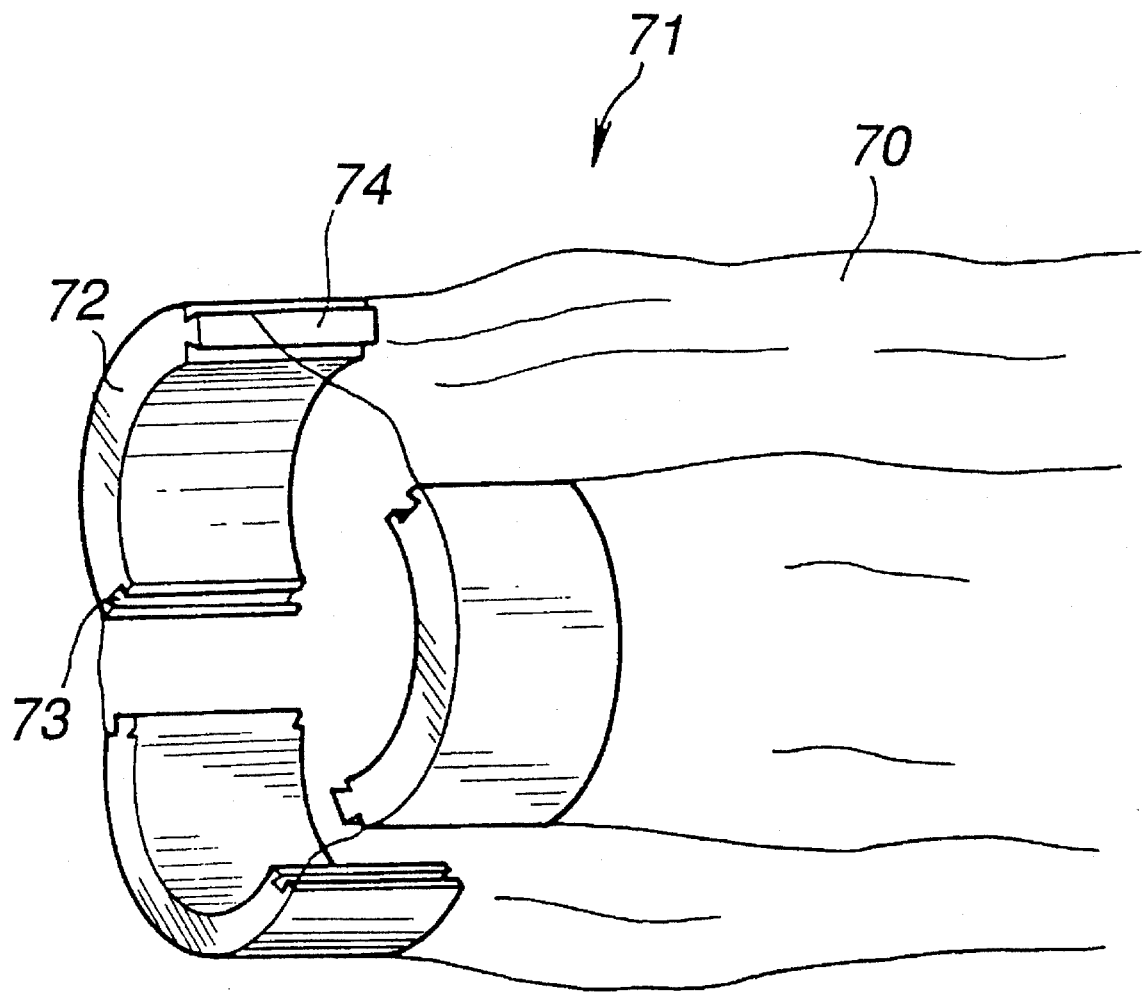

As illustrated in FIG. 10, a universal cord cover 70 provided by way of a modified example is constructed of a cover 71 and fixing members 72. The cover 71 is composed of a cylindrical soft plastic material. The fixing members 72 are provided on the inner peripheral surface of the end portion thereof. The fixing members 72 are a plurality of segments, each assuming a fan shape in section, of an annular hard plastic material to have a minor diameter smaller than a major diameter of the fixing groove on the side of the universal cord. A projection 74 and an engagement groove 73 which engage with each other are formed on and in connecting surfaces of adjacent fixing members 72. The fixing members 72 are allocated substantially uniformly along the inner peripheral surface of the end portion of the cover 71. An outer periphery of each of the fixing members 72 is bonded to the inner surface of the cover 71.

The universal cord cover 70 is covered from the other end of the connecting proximal part 45 (see FIG. 5(a)) of the universal cord 13B. At this moment, the fixing members 72 have been already segmented, and the end portion of the cover 71 is therefore opened wide. Just when the end portion of the cover 71 comes to the fixing groove 46, the projection 74 and the engagement groove 73 of the respective fixing members 72 are so connected as to be covered on the fixing groove 46, thus fixing the end portion.

In the universal cord cover 70 thus shown by way of the modified example, the fixing members 72 are manufactured in the form of plastic molded parts. Hence, reductions both in price and in weight can be attained.

Next, a second embodiment will be discussed. The second embodiment is substantially the same as the first embodiment except that a different arrangement is to be explained. The same components are marked with the like symbols, and the explanation is therefore omitted.

Figure 11:
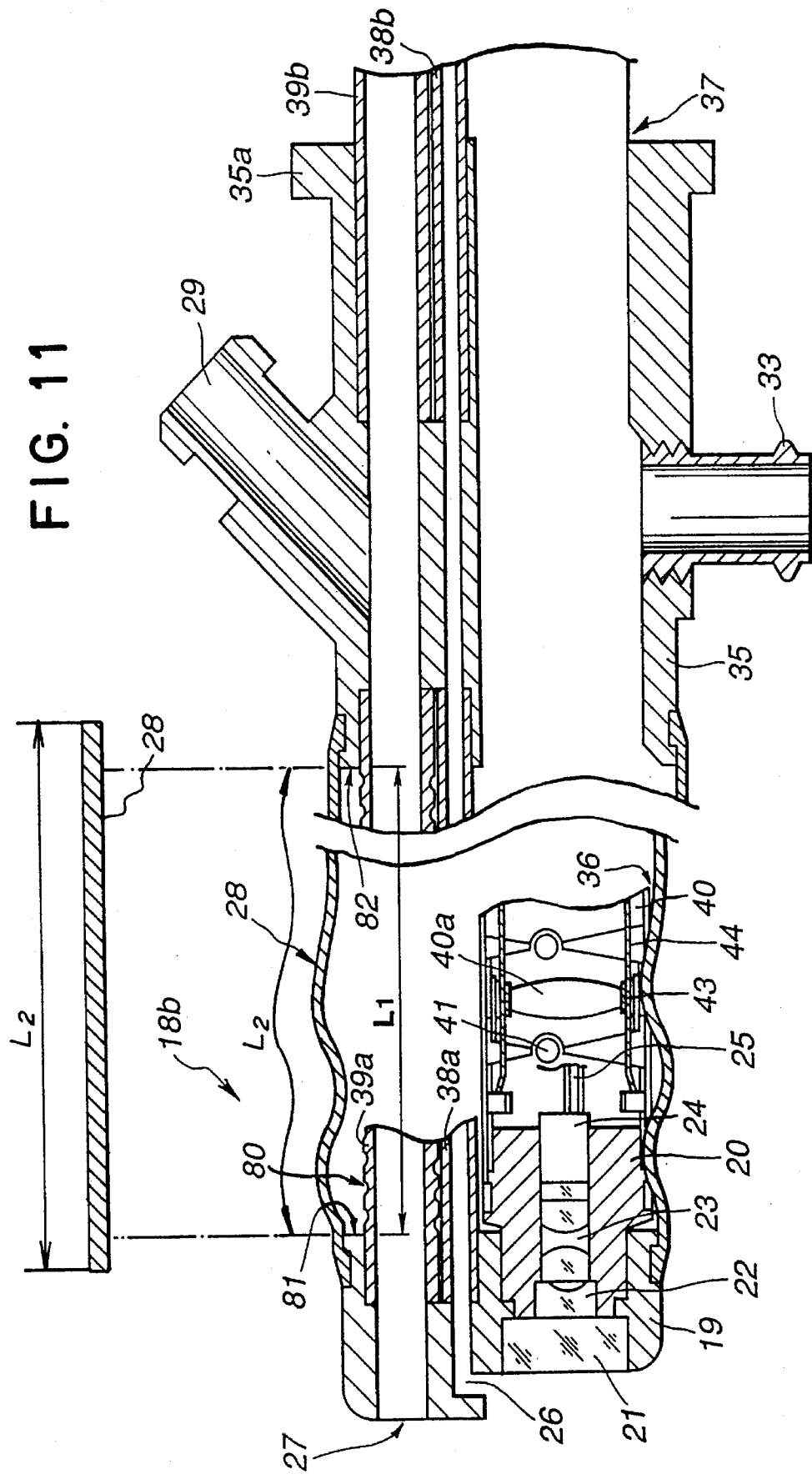
FIG. 11 is a sectional view illustrating a configuration of the principal portion of the cover endoscope in a second embodiment.

As illustrated in FIG. 11, the tip part 18b of the insert part covering section in the second embodiment is constructed as follows. A first air supply conduit 38a, a water supply conduit (not shown) and a channel 39a are connected to the distal end constructive part 19. The rear ends thereof are connected to an endoscope manipulation part fixing mouth part 35a. A helical groove 80 is cut in the outer peripheral surface of the channel 39a. Further, a second air supply conduit 38b, a water supply conduit (not illustrated) and a channel 39b are protruded from the rear end of the endoscope manipulation part fixing mouth part 35a. A distance L2 of the cover sheath 28 is set slightly larger than a distance L1 of each of the air supply conduit 38a, water supply conduit (not shown) and channel 39a between a rear end surface 81 of the distal end constructive part 19 and a front end surface 82 of the endoscope manipulation part fixing mouth part 35a. Other configurations and operations are the same as those in the first embodiment.

According to the cover system endoscope apparatus thus constructed in the second embodiment, the helical groove is formed in the channel within the insert part covering section. Hence, there is no possibility of reducing the flexibility of the covering section as a whole even when enhancing the rigidity of the channel for improving the resistance against buckling of the covering section. There is also no possibility of deteriorating the insertability because of consequently losing the flexibility balance of the cover endoscope when installed.

Further, the distance L2 of the cover sheath is set longer than the distance L1 of the conduit such as the channel, etc. The ease of installing the cover endoscope does not worsen due to slackening of the conduit like the channel in the covering section.

Next, a third embodiment will be discussed. The third embodiment is substantially the same as the first embodiment, only a different configuration will be explained. The same components are marked with the like symbols, and the description is therefore omitted.

Figure 12:
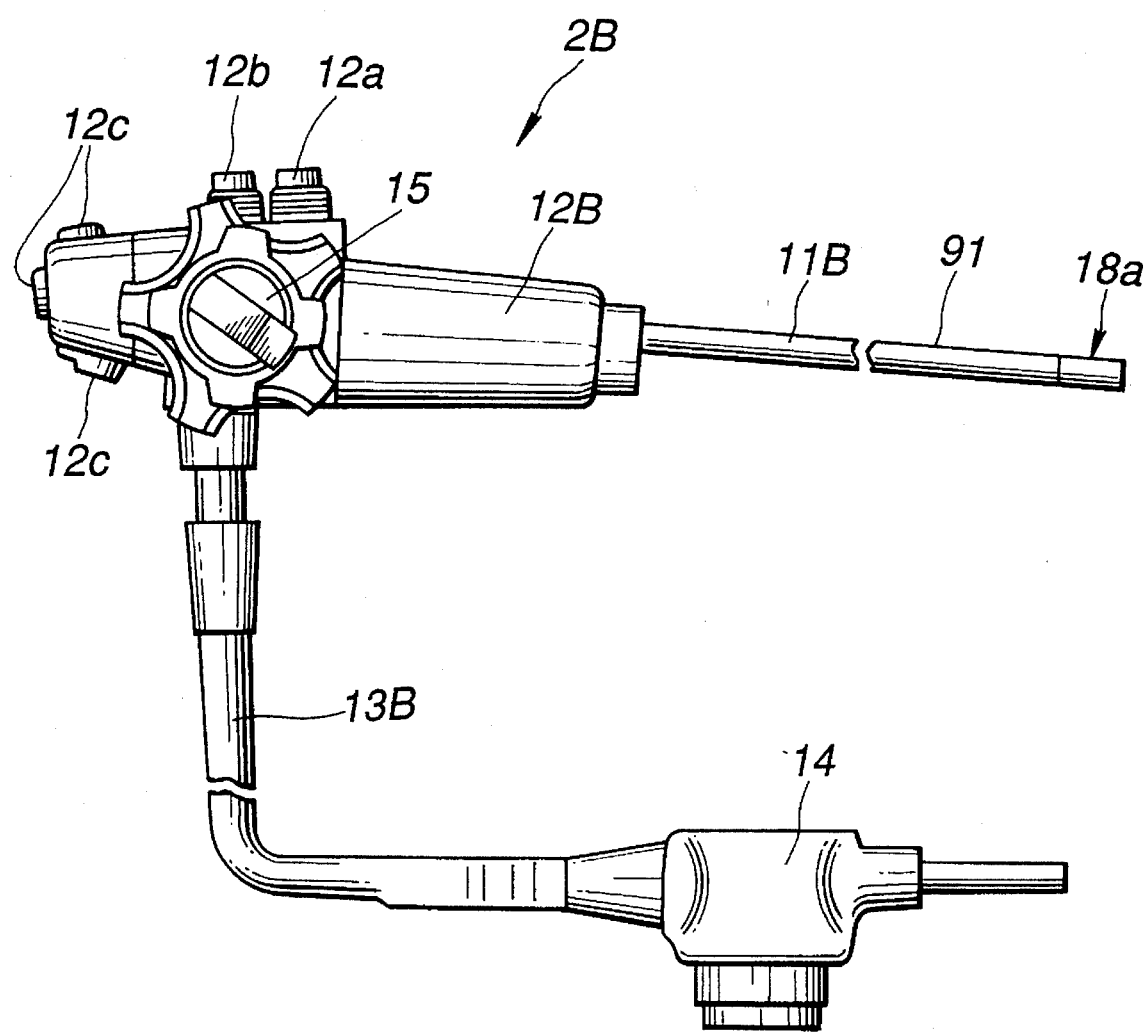
FIGS. 12 through 14 are related to a third embodiment.

As illustrated in FIG. 12, solely-water-soluble high polymers 91 are combined by graft polymerization on the outer surface of an insert part 11B.

Figure 13:
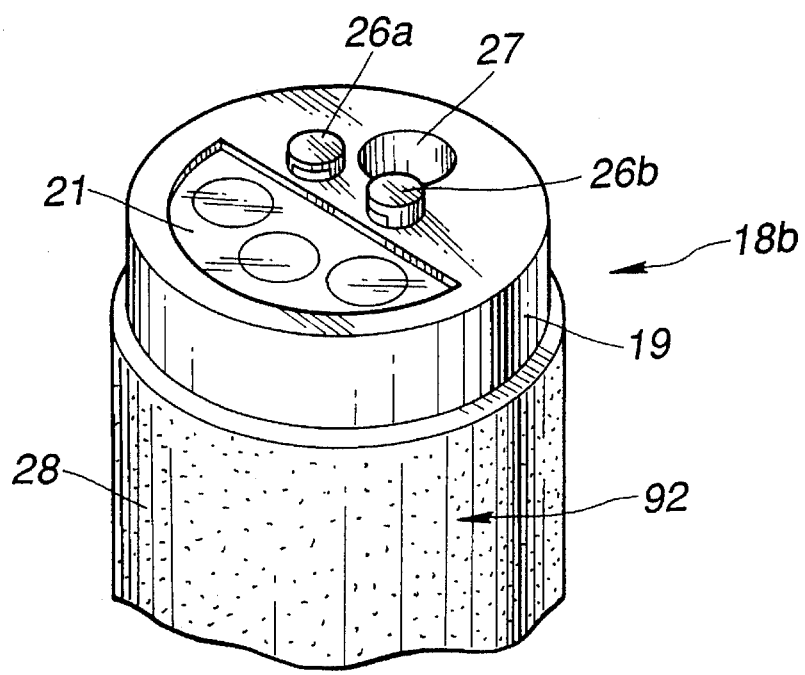

The tip part 18b of the insert part covering section 11A is, as illustrated in FIG. 13, formed of the distal end constructive part 19. The tip part 18b includes a transparent cover viewing window 21 corresponding to the semi-circular shape of the tip part 18a of the cover endoscope 2B as shown in FIG. 3. The tip part 18b further includes an air supply nozzle 26a, a water supply nozzle 26b opened to the cover viewing window 21 and a forceps outlet 27. Connected airtightly to this distal end constructive part 19 is an insert part cover sheath 28 for isolating the insert part 11B of the cover endoscope 2B from the external environment. This insert part cover sheath 28 is composed of a tube in which the solely-water-soluble high polymers 92 are combined by the graft polymerization on the outer surface of a soft resin such as polyurethane exhibiting an excellent chemical resistance and a relatively high flexibility.

Figure 14:
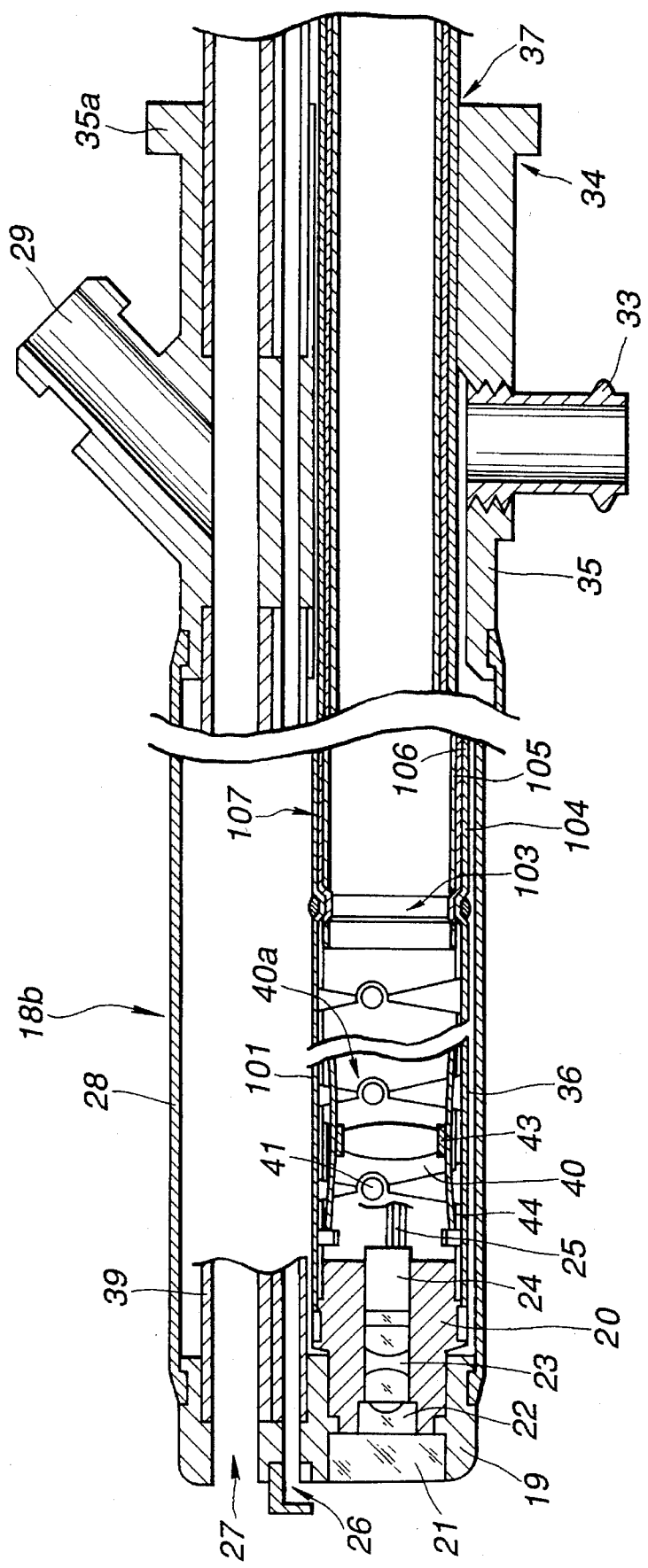

A near-at-hand portion 35a of the endoscope manipulation part fixing mouth part 35 is, as shown in FIG. 14, formed with an opening 37 of an endoscope insert channel 36 provided inwardly of the insert part cover sheath 28. Further, the distal end of the endoscope manipulation part fixing mouth part 35 is connected to the distal end constructive part 19 of the cover. Protruded are conduits such as an air supply conduit 38, a water supply conduit (though not illustrated) respectively communicating with the air supply nozzle 26a and the water supply nozzle 26b and also a channel 39 communicating with the forceps outlet 27. The ends of the near-at-hand portions of the air supply conduit 38 and the water supply conduit are herein connected to unillustrated air/water supply sources (not illustrated). These conduits are each composed of a soft resin such as PTFE or the like exhibiting a low flexibility and a relatively high flexural rigidity.

The outer periphery of a bendable part 40 is covered with a tubular bendable rubber 101 that is soft and stretchable. Connected via a connecting tube 103 to the rear end of the bendable part 40 is a flexible tubular part 107 consisting of a metallic band-like helical tube 104, a cylindrical steel tube 105 and an insert part sheath 106 formed of a soft resin. The rear end of the flexible tubular part 107 is connected to a manipulation part 12.

Note that a flexibility is given to each of the conduits such as the air supply conduit 38, the water supply conduit (not shown) and the channel 39 and also the insert part covering section 11A incorporating these conduits, and this flexibility is set larger than a flexibility of the flexible tubular part 107 of the cover endoscope 2B that is inserted into the endoscope insert channel 36.

Herein, the insert part cover sheath 28 is formed of a soft resin which is very thin, e.g., 0.2 mm, and therefore exhibits a large flexibility. Besides, the air supply conduit 38, the water supply conduit (not illustrated) and the channel 39 are preferably made of Teflon. These conduits each have a small diameter and are therefore large in terms of flexibility. For instance, the air supply conduit 38 and the water supply conduit (not shown) each have a minor diameter of 1.2 mm and a thickness of 0.3 mm. The channel 39 has a minor demeter of 2.8 mm and a thickness of 0.45 mm. On this assumption, a relationship in the magnitude of flexibility between these conduits is given such as:

Channel 39<Air supply conduit 38=Water supply conduit<Insert part cover sheath 28

On the other hand, for example, the band-like helical tube 104 of the flexible tubular part 107 is formed of stainless steel to have a thickness of 1.0 mm. The cylindrical steel tube 105 is formed of a polyimide resin, and a strand is 0.12 mm. Further, the insert part sheath 106 is composed of polystyrene and is 0.6 mm in thickness. The insert part sheath 106 permeates and is solidified in a gap of the cylindrical steel tube 105. The total flexibility of the flexible tubular part 107 is smaller than that of the insert part covering section 11A. Other configurations are the same as those in the first embodiment.

The following is an explanation of the operation of the thus constructed cover system endoscope apparatus.

As in the typical endoscope cover fitting method, the insert part covering section 11A is taken out of the storage package of the cover (not illustrated) containing the antibacterial endoscope cover 2A.

When inserting the cover endoscope 2B into the insert part covering section 11A, a flange of the upper end of the endoscope manipulation part fixing mouth part 35 is held in the semicircular holding part 10a (see FIG. 1) formed in the cover holding tool 10. In this state, the insert part 11B of the cover endoscope 2B is inserted from the endoscope manipulation part fixing mouth part 35. Thus, an easy installation can be done. At this time, a small amount of water content is added to the insert part 11B of the cover endoscope 2B. Graft chains of water-soluble high polymers 91 combined on the outer surface of the insert part 11B take in the water content and change into a well-lubricated slimy state. This facilitates the insertion thereof.

After installing the endoscope cover 2A, the insert part cover section 11A including the insert part 11B is inserted into the patient's body. At this moment, the graft chains of water-soluble high polymers 92 combined on the surface of the insert part cover sheath 28 taken in a body fluid enough to assume the well-lubricated slimy state. The insertion into the body cavity is thus facilitated. Other operations are the same as those in the first embodiment.

As discussed above, according to the cover system endoscope apparatus in this embodiment, the flexibility of the insert part covering section 11A is set higher than the flexibility of the flexible tubular part 107 of the cover endoscope 2A that is inserted into the endoscope insert channel 36. Namely, the conduits such as the air/water supply conduits and the channel in the insert part covering section 11A are more flexible than the insert part 11B of the cover endoscope 2A. Accordingly, the air/water supply conduits and the channel are not broken previously owing to the flexural manipulation during the insertion of a part of the cover system endoscope apparatus into the body cavity.

Further, the respective conduits are made confluent in the vicinity of the distal end constructive part, and the air and water are supplied via one nozzle provided at the tip. This conventional system is intricate in terms of structure of the confluent portions and is high in price. The conventional system is not suited to the insert part cover on the premise of the disposable application. In accordance with this embodiment, however, there are provided conduits dedicated to the supply of water and air, respectively. These conduits are independently connected to the nozzle of the distal end constructive part. This arrangement makes easy the control through the electromagnetic valve as well as decreasing the price.

Note that the water-soluble high polymers 91 are combined by the Graft polymerization on the outer surface of the insert part 11B to improve the insertability of the insert part 11B. The present invention is not, however, limited to this arrangement. The water-soluble high polymers may be Graft-combined on the inner surface of the insert part cover sheath 28. In addition, these two arrangements may be employed in combination. The combinational use further ameliorates the insertability of the endoscope insert part.

Next, a fourth embodiment will be discussed. The fourth embodiment is substantially the same as the third embodiment. The same components are marked with like symbols, and the description is therefore omitted.

Figure 15:
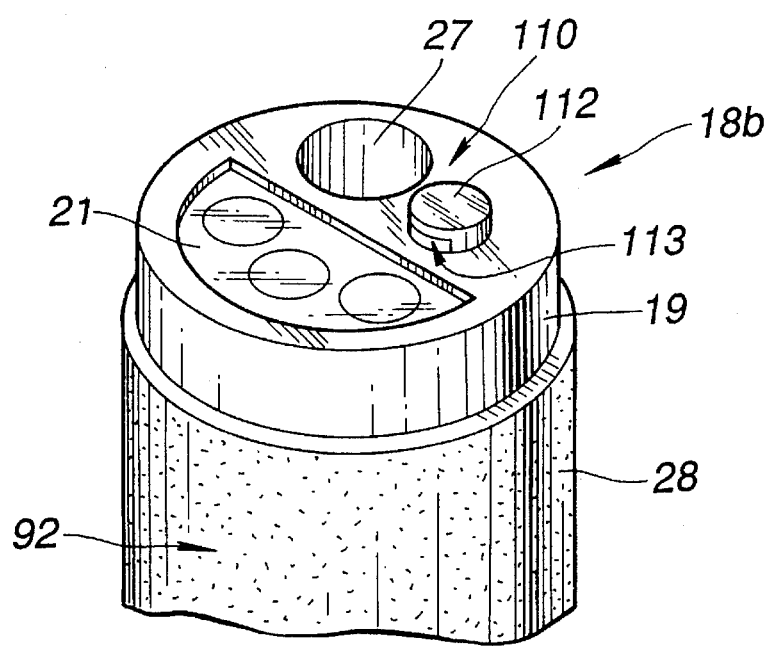

As illustrated in FIG. 15, the tip part 18b of the insert part covering section in the fourth embodiment consists of the distal end constructive part 19. The tip part 18b includes the transparent viewing window 21 corresponding to the semicircular shape of a distal end constructive part 20 of the cover endoscope 2B as shown in FIG. 3. The tip part 18b further includes an air/water supply nozzle 110 opened to the viewing window 21 and a forceps outlet 27. The air/water supply nozzle 110 is embedded in the tip surface of the distal end constructive part 19. Only a nozzle end portion 112 is protruded from the tip surface, and an opening 113 is directed to the viewing window 21.

Figure 16A:
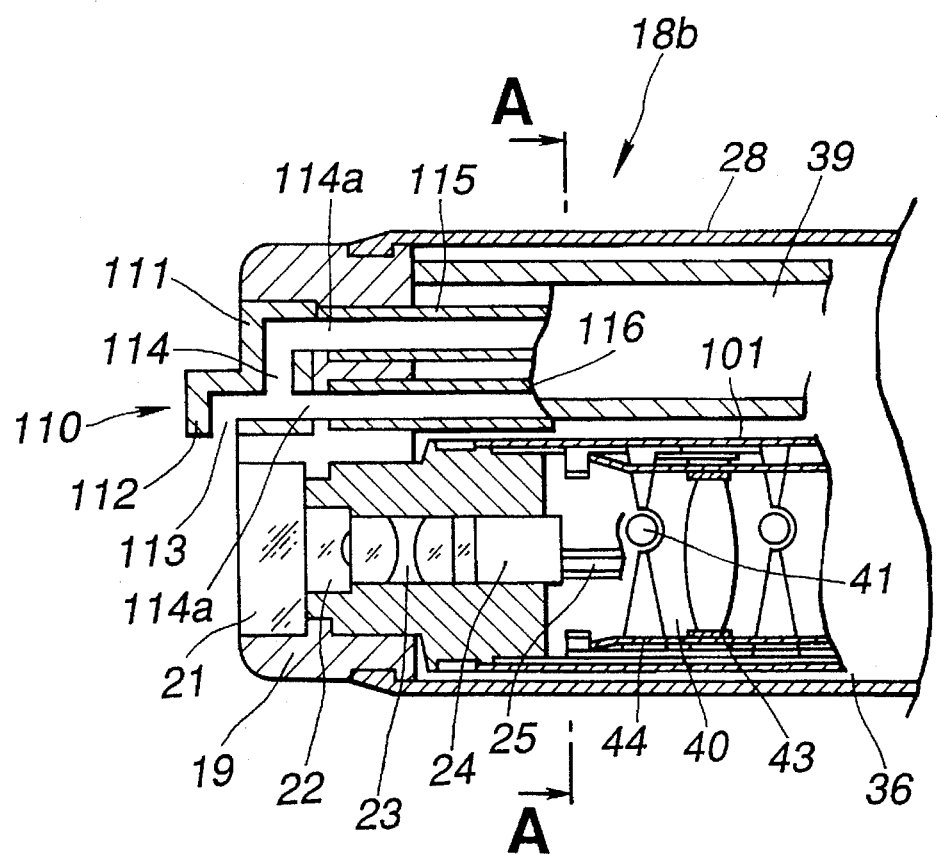
FIGS. 16(a)–(b) are sectional views showing a configuration of the principal portion of the cover endoscope.

As shown in FIG. 16(a), the air/water supply nozzle 110 consists of a base part 111 taking an elliptical shape in section and the nozzle end portion 112. The air/water supply nozzle 110 has a branch conduit 114 branching off in two ways in the base part 111 so as to communicate the opening 113 of the nozzle end portion 112. The rear end of the branch conduit 114 communicates with an air supply conduit 115 and a water supply conduit 116 connected to the distal end constructive part 19 via a connecting conduit 114a provided in the distal end constructive part 19.

Figure 16B:
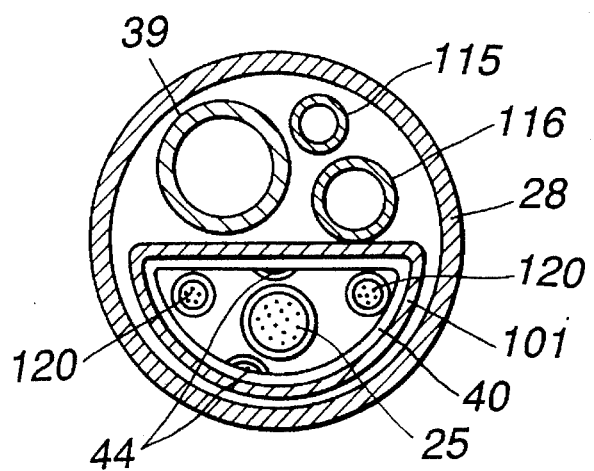

As shown in FIG. 16(b), a diameter of the water supply conduit 116 with a high-viscosity fluid flowing therethrough is larger than a diameter of the air supply conduit 115. The water supply conduit 116 having the larger diameter is disposed closer to the cross-sectional center of the insert part covering section 11A than the air supply conduit 115. Near-at-hand portions of the air and water supply conduits. 115, 116 are connected to air and water supply sources (not illustrated). Further, the air and water supply conduits 115, 116 are provided on the same side as the channel 39 to extend along the channel 39 communicating with the forceps outlet 27 and accommodated in the tip part cover. Incidentally, the numeral 120 designates a light guide for transmitting the illumination light to an illumination optical system 20a.

Other configurations and operations are the same as those in the third embodiment.

According to the cover system endoscope apparatus of the fourth embodiment, the following advantages are given in addition to those in the third embodiment. The air and water supply conduits are disposed in the side-by-side relationship on the same side as the channel. It is therefore possible to miniaturize and simplify the confluent structure of the conduits at the tip part. Besides, the conduit having the larger diameter is disposed closer to the cross-sectional center of the insert part covering section. An in-cover filling rate increases enough to reduce the diameter of the cover section.

It is apparent that, according to this invention, a wide range of different working modes can be formed based on the invention without deviating from the spirit and scope of the invention. This invention is not restricted by its specific working modes except by the appended claims.

What is claimed is:

1. A cover system endoscope apparatus comprising:

an endoscope; and an endoscope cover for covering said endoscope, said endoscope cover including:

a distal end constructive part;

a proximal end constructive part; and a soft tubular member through which said distal end constructive part and said proximal end constructive part are airtightly connected,.

wherein said tubular member has a soft channel tube provided in the interior thereof, and wherein a first total distance resulting from adding a first distance from an end of said distal end constructive part to a first end of said tubular member, a second distance measured along a surface of said tubular member from the first end to the second end of said tubular member, and a third distance from a second end of said tubular member to an end surface of said proximal end constructive part member to an end surface of said proximal end constructive part is greater than a second total distance resulting from adding said first distance from an end of said distal end constructive part to the first end of said tubular member, a fourth distance measured along a surface of said channel tube from the first end to the second end of said tubular member, and said third distance from a second end of said tubular member to the end surface of said proximal end constructive part.

2. The cover system endoscope apparatus according to claim 1, wherein watersoluble high polymers are graft-combined on a part of a contact surface between an insert part of said endoscope and said endoscope cover.

3. The cover system endoscope apparatus according to claim 1, wherein water-soluble high polymers are graft-combined on a part of an outer surface of said tubular member.

4. The cover system endoscope apparatus according to claim 1, wherein a bladder-like overcoat tube is covered on said endoscope to close one end, and a medical lubricating agent is sealed between said overcoat tube and said endoscope cover.

5. The cover system endoscope apparatus according to claim 1, further comprising a cover including a cylindrical bladder composed of a soft plastic material and having its two ends opened and a plurality of splittable segments provided leastwise at one end of an opening and assuming an annular shape when combined.

6. The cover system endoscope apparatus according to claim 5, wherein said segments are each composed of a magnetic material.

7. The cover system endoscope apparatus according to claim 5, wherein surfaces facing each other when combined of said segments, respectively, have projections and engagement grooves that engage with each other.

8. A cover system endoscope apparatus according to claim 1, wherein a rigidity of said soft channel tube is greater than a rigidity of said tubular member.

9. A cover system endoscope apparatus according to claim 1, wherein a flexibility of said soft channel tube is greater than a flexibility of a flexible tube of an insert part of said endoscope.

10. A cover system endoscope apparatus according to claim 1, wherein said endoscope has a bending mechanism for bending a tip part of an insert part, wherein said bending mechanism adjusts a maximum bending angle of said tip part of said insert part so that the maximum bending angle of said tip part of said cover endoscope in said endoscope cover system becomes a predetermined bending angle.

* * * * *

UNITED STATES PATENT AND TRADEMARK OFFICE
CERTIFICATE OF CORRECTION

PATENT NO. : 5,514,074
DATED : May 7, 1996
INVENTOR(S) : Hisao YABE, et al.

It is certified that error appears in the above-indentified patent and that said Letters Patent is hereby corrected as shown below:

Column 14, lines 12 and 13, delete "to an end surface of said proximal end constructive part member".

Signed and Sealed this

Fifteenth Day of October, 1996

Attest:

BRUCE LEHMAN

Attesting Officer   Commissioner of Patents and Trademarks